(12) United States Patent
Gerrans et al.

(10) Patent No.: US 9,186,485 B2
(45) Date of Patent: *Nov. 17, 2015

(54) NESTED BALLOON CATHETER FOR LOCALIZED DRUG DELIVERY

(71) Applicants: Lawrence J. Gerrans, San Anselmo, CA (US); Erhan H. Gunday, Great Neck, NY (US)

(72) Inventors: Lawrence J. Gerrans, San Anselmo, CA (US); Erhan H. Gunday, Great Neck, NY (US)

(73) Assignee: Sanovas, Inc., San Rafael, CA (US)

( * ) Notice: Subject to any disclaimer, the term of this patent is extended or adjusted under 35 U.S.C. 154(b) by 84 days.

This patent is subject to a terminal disclaimer.

(21) Appl. No.: 13/715,654

(22) Filed: Dec. 14, 2012

(65) Prior Publication Data

US 2013/0165769 A1   Jun. 27, 2013

Related U.S. Application Data

(63) Continuation of application No. 13/037,856, filed on Mar. 1, 2011, now Pat. No. 8,348,890.

(51) Int. Cl.
*A61M 25/00* (2006.01)
*A61M 25/10* (2013.01)
*A61M 5/00* (2006.01)
*A61B 5/06* (2006.01)
*A61N 5/06* (2006.01)
(Continued)

(52) U.S. Cl.
CPC ............ *A61M 25/1011* (2013.01); *A61B 5/065* (2013.01); *A61M 5/007* (2013.01); *A61B 5/021* (2013.01); *A61B 5/4839* (2013.01); *A61M 25/1018* (2013.01); *A61M 2025/105* (2013.01); *A61M 2025/1013* (2013.01); *A61M 2025/1052* (2013.01); *A61M 2025/1086* (2013.01); *A61N 5/0603* (2013.01); *A61N 5/1014* (2013.01)

(58) Field of Classification Search
CPC ............... A61M 2025/105; A61M 2025/1086; A61M 2025/0057; A61M 37/0015; A61M 2025/1031
USPC ........................... 604/101.01, 101.02, 102.01
See application file for complete search history.

(56) References Cited

U.S. PATENT DOCUMENTS

| 4,186,745 A | 2/1980 | Lewis et al. |
| 4,446,867 A | 5/1984 | Leveen et al. |

(Continued)

FOREIGN PATENT DOCUMENTS

| EP | 1230944 A2 | 8/2002 |
| EP | 1913882 A1 | 4/2008 |

(Continued)

*Primary Examiner* — Aarti B Berdichevsky
(74) *Attorney, Agent, or Firm* — St. Onge Steward Johnston & Reens LLC (57) ABSTRACT

A balloon catheter for delivering a therapeutic and/or diagnostic agent to tissue is described including an outer balloon having a wall with an opening therethrough and an inner surface, an inner balloon disposed in the outer balloon, enclosing an inflation chamber and having an outer surface defining a space between the outer surface of the inner balloon and the inner surface of the outer balloon, a catheter having a first lumen in fluid communication with the space between the inner balloon and the outer balloon for supplying the agent thereto, and a second lumen through which fluid is supplied to the inflation chamber for inflating the inner balloon to urge the agent out of the opening in the outer balloon, wherein the outer balloon and/or the inner balloon comprise at least one protrusion for directing the agent formed by an inner balloon wall and/or the outer balloon wall.

43 Claims, 8 Drawing Sheets

(51) Int. Cl.
  *A61N 5/10* (2006.01)
  *A61B 5/021* (2006.01)
  *A61B 5/00* (2006.01)

(56) References Cited

U.S. PATENT DOCUMENTS

| | | |
|---|---|---|
| 4,773,899 A | 9/1988 | Spears |
| 4,824,436 A | 4/1989 | Wolinsky |
| 4,921,484 A | 5/1990 | Hillstead |
| 4,994,033 A | 2/1991 | Shockey et al. |
| 5,049,132 A | 9/1991 | Shaffer et al. |
| 5,100,425 A | 3/1992 | Fischell et al. |
| 5,196,017 A | 3/1993 | Silva et al. |
| 5,304,121 A | 4/1994 | Sahatjian et al. |
| 5,304,220 A | 4/1994 | Maginot |
| 5,336,234 A | 8/1994 | Vigil et al. |
| 5,397,307 A | 3/1995 | Goodin |
| 5,545,133 A | 8/1996 | Burns et al. |
| 5,611,775 A | 3/1997 | Machold et al. |
| 5,647,847 A | 7/1997 | Lafontaine et al. |
| 5,674,192 A | 10/1997 | Sahatjian et al. |
| 5,707,352 A | 1/1998 | Sekins et al. |
| 5,728,064 A | 3/1998 | Burns et al. |
| 5,785,685 A | 7/1998 | Kugler et al. |
| 5,833,644 A | 11/1998 | Zadno-Azizi et al. |
| 5,873,852 A | 2/1999 | Vigil et al. |
| 6,024,693 A | 2/2000 | Schock et al. |
| 6,048,332 A | 4/2000 | Duffy et al. |
| 6,129,705 A | 10/2000 | Grantz |
| 6,190,354 B1 | 2/2001 | Sell et al. |
| 6,245,008 B1 | 6/2001 | Leschinsky et al. |
| 6,248,092 B1 | 6/2001 | Miraki et al. |
| 6,440,158 B1 | 8/2002 | Saab |
| 6,485,500 B1 | 11/2002 | Kokish et al. |
| 6,544,221 B1 | 4/2003 | Kokish et al. |
| 6,616,597 B2 | 9/2003 | Schock et al. |
| 6,623,452 B2 | 9/2003 | Chien et al. |
| 6,685,648 B2 | 2/2004 | Flaherty et al. |
| 6,733,459 B1 | 5/2004 | Atsumi |
| 7,014,652 B2 | 3/2006 | Cioanta et al. |
| 7,025,718 B2 | 4/2006 | Williams |
| 7,462,165 B2 | 12/2008 | Ding et al. |
| 7,470,252 B2 | 12/2008 | Mickley et al. |
| 7,569,032 B2 | 8/2009 | Naimark et al. |
| 7,611,484 B2 | 11/2009 | Wellman et al. |
| 7,658,966 B2 | 2/2010 | Kokish |
| 7,727,226 B2 | 6/2010 | Chang et al. |
| 7,935,044 B2 | 5/2011 | Lubock |
| 8,182,446 B2 | 5/2012 | Schaeffer et al. |
| 2003/0065303 A1 | 4/2003 | Wellman et al. |
| 2003/0114791 A1 | 6/2003 | Rosenthal et al. |
| 2004/0044308 A1 | 3/2004 | Naimark et al. |
| 2004/0064093 A1 | 4/2004 | Hektner et al. |
| 2005/0015049 A1 | 1/2005 | Rioux et al. |
| 2005/0107741 A1 | 5/2005 | Willard et al. |
| 2006/0200074 A1 | 9/2006 | Zadno-Azizi |
| 2007/0060942 A2 | 3/2007 | Zadno-Azizi |
| 2008/0039791 A1 | 2/2008 | Abboud et al. |
| 2008/0051627 A1 | 2/2008 | Raju |
| 2008/0171985 A1 | 7/2008 | Karakoca |
| 2008/0208118 A1 | 8/2008 | Goldman |
| 2009/0105687 A1 | 4/2009 | Deckman et al. |
| 2009/0171268 A1 | 7/2009 | Williams, Jr. et al. |
| 2009/0229374 A1 | 9/2009 | Carlisle et al. |
| 2009/0254064 A1 | 10/2009 | Boatman |
| 2010/0069900 A1 | 3/2010 | Shirley et al. |
| 2010/0113939 A1 | 5/2010 | Mashimo et al. |
| 2010/0121270 A1 | 5/2010 | Gunday et al. |
| 2011/0082483 A1 | 4/2011 | Diamant et al. |
| 2011/0152683 A1 | 6/2011 | Gerrans et al. |
| 2011/0166516 A1 | 7/2011 | Orr |
| 2011/0218494 A1 | 9/2011 | Gerrans et al. |
| 2012/0095292 A1 | 4/2012 | Gunday et al. |

FOREIGN PATENT DOCUMENTS

| | | |
|---|---|---|
| WO | 9304727 A1 | 3/1993 |
| WO | 2009046206 A1 | 4/2009 |
| WO | 2009086269 A2 | 7/2009 |
| WO | 2010024871 A1 | 3/2010 |

NESTED BALLOON CATHETER FOR LOCALIZED DRUG DELIVERY

FIELD OF THE INVENTION

The present invention relates to methods and systems for delivering therapeutic and/or diagnostic agents to specific cellular locations within and adjacent to bodily tissues and cavities. More specifically, the invention relates to a method and system of localized delivery of diagnostic and/or therapeutic agents to bodily tissues and cavities via a nested balloon catheter.

BACKGROUND OF THE INVENTION

In diagnosing and treating diseases of various body cavities and organs, it is necessary to deliver diagnostic and/or therapeutic agents to the organs at specified locations. Most common routes of drug delivery include a non-invasive peroral (through the mouth), topical (skin), transmucosal (nasal, buccal/sublingual, vaginal, ocular and rectal) and inhalation routes. However, many therapeutic and diagnostic agents in general may not be delivered using these routes because they might be susceptible to enzymatic degradation or cannot be absorbed into the systemic circulation efficiently due to molecular size and charge issues, and thus, will not be therapeutically effective. For this reason, many such drugs have to be delivered by injection.

There are several known problems associated with the injection process. One of such problems is undesirable extravasation of the diagnostic or therapeutic agents into tissue, which is particularly prevalent with intravenously injected agents. Extravasation generally refers to leakage of fluids out of a container, and more specifically refers to leakage of intravenous drugs from a vein into surrounding tissues, resulting in an injury to the tissues. Once the intravenous extravasation has occurred, damage can continue for months and involve nerves, tendons and joints. If treatment is delayed, surgical debridement, skin grafting, and even amputation have been known to be the unfortunate consequences.

Occurrence of extravasation is possible with all intravenous drugs, but it is a particularly significant problem with cytoxic drugs used for treatment of cancer (i.e. during chemotherapy).

Chemotherapy is the general term for any treatment involving the use of chemical agents to stop cancer cells from growing. Chemotherapy can eliminate cancer cells at sites great distances from the original cancer. As a result, chemotherapy is considered a systemic treatment. More than half of all people diagnosed with cancer receive chemotherapy. A chemotherapy regimen (a treatment plan and schedule) usually includes drugs to fight cancer plus drugs to help support completion of the cancer treatment.

Chemotherapy can be administered through a vein, injected into a body cavity, or delivered orally in the form of a pill, depending on which drug is used. Chemotherapy works by destroying cancer cells. Unfortunately, it cannot tell the difference between a cancer cell and some healthy cells. Thus, chemotherapy often eliminates not only the fast-growing cancer cells, but also other fast-growing cells in the body, including hair and blood cells. Some cancer cells grow slowly while others grow rapidly. As a result, different types of chemotherapy drugs target the growth patterns of specific types of cancer cells.

Each chemotherapy drug works differently and is effective at a specific time in a life cycle of the cell it targets. Brachytherapy, sometimes called seed implantation, is an outpatient procedure used in the treatment of different kinds of cancer. The radioactive "seeds" are carefully placed inside of the cancerous tissue and positioned in a manner that will attack the cancer most efficiently. The radioactive seeds are about the size of a grain of rice, and give off radiation that travels only a few millimeters to kill nearby cancer cells. There are two different kinds of brachytherapy: permanent, when the seeds remain inside the body, and temporary, when the seeds are inside of the body and are then removed. With permanent implants (e.g. prostate), the radioactivity of the seeds typically decays with time.

The other type of chemotherapy is when cytotoxic agents are delivered intravenously. Veins of people receiving chemotherapy are often fragile, mobile, and difficult to cannulate. Patients who receive chemotherapy at the same site as radiotherapy may experience a reactivation of skin toxicity known as a "recall" phenomenon. Patients who have had previous radiation therapy at the site of injection may develop severe local reactions from cytotoxic drugs. Cytotoxic drugs also have the potential to cause cutaneous abnormalities in areas that have been damaged previously by radiation, even in areas that are distant from the injection site. Patients who receive further chemotherapy in a different site may experience an exacerbation of tissue damage in the original site.

Furthermore, areas of previous surgery where the underlying tissue is likely to be fibrosed and toughened dramatically present an increased risk of extravasation. Radical mastectomy, axillary surgery or lymph node dissection may impair circulation in a particular limb. This reduces venous flow and may allow intravenous solutions to pool and leak around the site of cannulation.

Some chemotherapy drugs often never reach the tumors they are intended to treat because the blood vessels feeding the tumors are abnormal. A tumor's capillaries (small blood vessels that directly deliver oxygen and nutrients to cancer cells) can be irregularly shaped, being excessively thin in some areas and forming thick, snarly clumps in others. These malformations create a turbulent, uneven blood flow, so that too much blood goes to one region of the tumor, and too little to another. In addition, the capillary endothelial cells lining the inner surface of tumor capillaries, normally a smooth, tightly-packed sheet, have gaps between them, causing vessel leakiness.

The systemic and intravenous side effects of chemotherapy coupled with the limited effect of systemic administration due to abnormal characteristics of tumor blood vessels have given the scientific community pause, in searching for more direct, localized and biologic solutions. Accordingly, the oncology literature has become increasingly populated with articles espousing prospective benefits and positive outcomes of intra-tumoral chemotherapy. A direct administration of cytotoxic drugs such as Mytomycin, Mytomycin-C, Bleomycin, Fluorouracil, Mitoxantrone, Cisplatin, and Avastin in endobronchial intra-tumoral chemotherapy has been done experimentally via direct injection of the agent into the endobronchial tumor. In these cases, the tumor was reported to have died and been subsequently removed.

However, while some experimental uses of the localized delivery of cytotoxic drugs have been attempted, there has been little implementation of such drug delivery in practice, possibly due to numerous problems associated with such delivery. First, it is often necessary to deliver cytotoxic drugs to remote and not easily accessible blood vessels and other lumens within body organs, such as lungs. It is also important to be able to deliver defined doses of the cytotoxic substances because such substances are often very expensive or are capable of causing serious harm if delivered in excess. More-over, the existing methods lack the ability to contain the cytotoxic agent and/or radiation therapy and mitigate collateral damage to non-affected anatomy and structures.

Several devices have been proposed for a targeted delivery of drugs to internal bodily cavities, such as those disclosed in U.S. Pat. No. 4,994,033 to Shokey et al and U.S. Pat. No. 5,049,132 to Shaffer et al. In these systems, a catheter is provided with an inner balloon and an outer balloon. The inner balloon is inflated to dilate a lesion in an affected blood vessel. The outer balloon is provided with openings, and the drug is ejected out of the openings and into the lesion as the inner balloon is inflated.

While useful for treatment of stenotic lesions, these systems are not particularly useful for other applications, such as treatment of cancerous tumors, and are not efficient at infusing the relevant biological material with the drug. Instead, the catheter may need to remain in place for an unnecessarily long period of time while the infusion of the drug into the biological material is allowed to take place. This is undesirable, especially in applications such as pulmonology, where the patient's respiratory passage has been somewhat restricted by the device. Further, this can result in some of the agent never being infused into the targeted material and instead remaining in the cavity and, after the balloon catheter is removed, subsequently migrating to other undesired portions of the body.

What is desired, therefore, is a balloon catheter system for delivering therapeutic and/or diagnostic agents to bodily tissues, tumors, and other biological materials that can locally deliver the agent to a specific target site. What is further desired is a balloon catheter system for delivering therapeutic and/or diagnostic agents that facilitates the infusion of the drug into surrounding bodily tissues, tumors, and other biological materials. What is also desired is a balloon catheter system for delivering therapeutic and/or diagnostic agents that can adjust for changing conditions during the process of delivering the drug.

SUMMARY OF THE INVENTION

Accordingly, it is an object of the present invention to provide a nested balloon catheter system that can deliver therapeutic and/or diagnostic agents to bodily tissues, tumors, and other biological materials from within bodily cavities.

It is a further object of the present invention to provide a nested balloon catheter system that can target specific areas for the delivery of therapeutic and/or diagnostic agents to bodily tissues, tumors, and other biological materials.

It is yet another object of the present invention to provide a nested balloon catheter system that facilitates infusion of therapeutic and/or diagnostic agents into surrounding bodily tissues, tumors, and other biological materials.

It is still another object of the present invention to provide a nested balloon catheter system for delivering therapeutic and/or diagnostic agents to bodily tissues, tumors, and other biological materials that provides physiological feedback from which the intra-lumen diameter of the bodily cavity can be determined, and the pressure and flow supplied to the balloon can be adjusted accordingly.

It is another object of the present invention to provide a nested balloon catheter system for delivering therapeutic and/or diagnostic agents to bodily tissues, tumors, and other biological materials that permits the passage of bodily fluids through the system.

It is yet another object of the present invention to provide a nested balloon catheter system for delivering therapeutic and/or diagnostic agents to bodily tissues, tumors, and other biological material that provides visualization from within the bodily cavity.

In order to overcome the deficiencies of the prior art and to achieve at least some of the objects and advantages listed, the invention comprises a balloon catheter for delivering a therapeutic and/or diagnostic agent to tissue including an outer balloon having a wall with at least one opening therethrough and an inner surface, and an inner balloon at least partially disposed in the outer balloon, at least partially enclosing an inflation chamber and having an outer surface defining a space between the outer surface of the inner balloon and the inner surface of the outer balloon. The balloon catheter further includes a catheter having a first lumen in fluid communication with the space between the outer surface of the inner balloon and the inner surface of the outer balloon for supplying a therapeutic and/or diagnostic agent thereto, and a second lumen through which fluid is supplied to the inflation chamber of the inner balloon for inflating the inner balloon to urge the therapeutic and/or diagnostic agent out of the at least one opening in the wall of the outer balloon and into tissue. At least one of the outer balloon and the inner balloon comprise at least one protrusion for directing the therapeutic and/or diagnostic agent.

In some embodiments, the wall of the outer balloon has an abrasive outer surface for abrading tissue.

In certain embodiments, the balloon catheter further includes a fluid source that supplies fluid to the second lumen of the catheter. In some of these embodiments, the fluid source is an electro-pneumatic pump. In certain of these embodiments, the pump supplies fluid to the inflation chamber in pulsed fashion to repeatedly deflate and inflate the inner balloon. In other embodiments, the fluid source further comprises a vacuum source that evacuates fluid from the inflation chamber.

In certain embodiments, the invention further includes a monitoring device for monitoring at least one patient vital sign, and the pump controls the pressure to which the inner balloon is inflated based at least in part on the monitored vital sign. In some embodiments, the invention includes a monitoring device for monitoring at least one patient vital sign, and the pump controls the supply of the therapeutic and/or diagnostic agent based at least in part on the monitored vital sign.

In some advantageous embodiments, the balloon catheter includes an imaging device disposed in the catheter for viewing tissue in a bodily cavity. In additional advantageous embodiments, the balloon catheter includes at least one imaging marker mounted adjacent to the inner and outer balloons.

In some embodiments, a distal end of the catheter has an opening therein and the catheter has a third lumen in fluid communication with the opening for passing bodily fluids through the catheter.

In certain embodiments, the balloon catheter includes at least one sensor for measuring at least one characteristic of tissue.

In some embodiments, the catheter further includes a distal balloon positioned distally of the inner and outer balloons and a proximal balloon positioned proximally of the inner and outer balloons, wherein the fluid source inflates the proximal balloon and the distal balloon by supplying fluid thereto to create a chamber therebetween. In some of these embodiments, an outer surface of the proximal and distal balloons has a textured surface for preventing slippage of the outer surface on tissue.

In certain advantageous embodiments, the fluid is a gas.

In some embodiments, the inner surface of the outer balloon includes at least one protrusion for directing the therapeutic and/or diagnostic agent. In other embodiments, the outer surface of the inner balloon includes at least one protrusion for directing the therapeutic and/or diagnostic agent. In additional embodiments, the outer balloon has an outer surface and the outer surface includes at least one protrusion for directing the therapeutic and/or diagnostic agent.

In additional advantageous embodiments, the inner surface of the outer balloon includes a first protrusion having a shape, and the outer surface of the inner balloon includes a second protrusion corresponding to the shape of the first protrusion to create a channel therebetween. In yet further embodiments, the outer surface of the inner balloon comprises a first protrusion and a second protrusion, the first and second protrusions extending longitudinally and forming a channel therebetween, wherein an outer surface of the outer balloon comprises a third protrusion having an annular shape, and wherein the at least one opening in the wall of the outer balloon is enclosed by the third annular protrusion.

In certain advantageous embodiments, the wall of the outer balloon has an outer surface comprising a mesh sleeve of elastic yarn. In some cases, the mesh sleeve is radiopaque.

The invention also comprises a balloon catheter for delivering a therapeutic and/or diagnostic agent to tissue, including an outer balloon having a wall with at least one opening therethrough and an inner surface, and an inner balloon at least partially disposed in the outer balloon, the inner balloon at least partially enclosing an inflation chamber and having an outer surface defining a space between the outer surface of the inner balloon and the inner surface of the outer balloon. The balloon catheter also includes a catheter having a first lumen in fluid communication with the inflation chamber of the inner balloon for supplying fluid thereto to inflate the inner balloon and a second lumen in fluid communication with the space between the outer surface of the inner balloon and the inner surface of the outer balloon for supplying a therapeutic and/or diagnostic agent thereto. The balloon catheter further includes a fluid source in fluid communication with the first lumen for inflating the inner balloon to urge the therapeutic and/or diagnostic agent out of the at least one opening in the wall of the outer balloon and into tissue, wherein the fluid source supplies fluid to the first lumen in pulsed fashion to repeatedly inflate and at least partially deflate the inner balloon.

The invention further comprises a method of localized delivery of a therapeutic and/or diagnostic agent to tissue, including the step of inserting a catheter into a bodily cavity, the catheter comprising an outer balloon having a wall with at least one opening therethrough and an inner surface, and an inner balloon at least partially disposed in the outer balloon, the inner balloon at least partially enclosing an inflation chamber and having an outer surface defining a space between the outer surface of the inner balloon and the inner surface of the outer balloon. The method also includes the steps of supplying the therapeutic and/or diagnostic agent to the space between the outer surface of the inner balloon and the inner surface of the outer balloon via a second lumen of the catheter, and inflating the inner balloon by supplying fluid to the inflation chamber via a first lumen of the catheter to urge the therapeutic and/or diagnostic agent out of the at least one opening in the wall of the outer balloon and into tissue. The method further includes the step of repeatedly deflating and inflating the inner balloon by supplying fluid to the inflation chamber in pulsed fashion.

In some embodiments, the wall of the outer balloon has an abrasive outer surface, and the step of inflating the inner balloon includes contacting tissue in the bodily cavity with the abrasive surface such that it abrades the tissue.

In certain embodiments, the step of delivering the therapeutic and/or diagnostic agent to tissue further includes inflating the inner balloon until the wall of the outer balloon contacts tissue in the bodily cavity.

In some advantageous embodiments, the step of inflating the inner balloon comprises supplying fluid thereto with an electro-pneumatic pump.

In certain embodiments, the method further includes monitoring at least one vital sign of a patient.

In certain advantageous embodiments, the method further includes the step of using an imaging device disposed in the catheter to visualize tissue in the bodily cavity. In other advantageous embodiments, the method further includes measuring at least one characteristic of tissue in the bodily cavity via at least one sensor.

In some embodiments, the agent is doxorubicin. In other embodiments, the agent is cisplatin, and the method further includes the step of supplying a second agent, the second agent being epinephrine. In further embodiments, the agent is 5-4 fluorouracil. In some embodiments, the agent is noscapine, and in some cases, the agent is diltiazem augment taxol. In other embodiments, the agent is crizotinib, gefitinib, or erlotinib hydrochloride. In some embodiments, the agent includes drug eluting microspheres, which in some cases, contain doxorubicin. In yet further embodiments, the agent is a combination of at least one therapeutic agent and at least one biomarker, and the method further includes the step of monitoring extravasation of the at least one therapeutic agent into tissue via the at least one biomarker. In some of these embodiments, the biomarker is a radio-opaque marker.

In certain embodiments, the catheter further includes a distal balloon positioned distally of the inner and outer balloons and a proximal balloon positioned proximally of the inner and outer balloons, wherein the method further includes the step of inflating the distal and proximal balloons by supplying fluid thereto via at least one additional lumen of the catheter to create a chamber between the distal and proximal balloons, and wherein the step of delivering the therapeutic and/or diagnostic agent includes delivering the agent to the chamber.

In some embodiments, the step of delivering the therapeutic and/or diagnostic agent further includes supplying the agent to a channel defined by a first protrusion provided on the inner surface of the outer balloon and a second protrusion provided on the outer surface of the inner balloon such that the agent is delivered to a localized area in the bodily cavity.

Other objects of the invention and its particular features and advantages will become more apparent from consideration of the following drawings and accompanying detailed description.

DETAILED DESCRIPTION OF THE INVENTION

Figure 1:
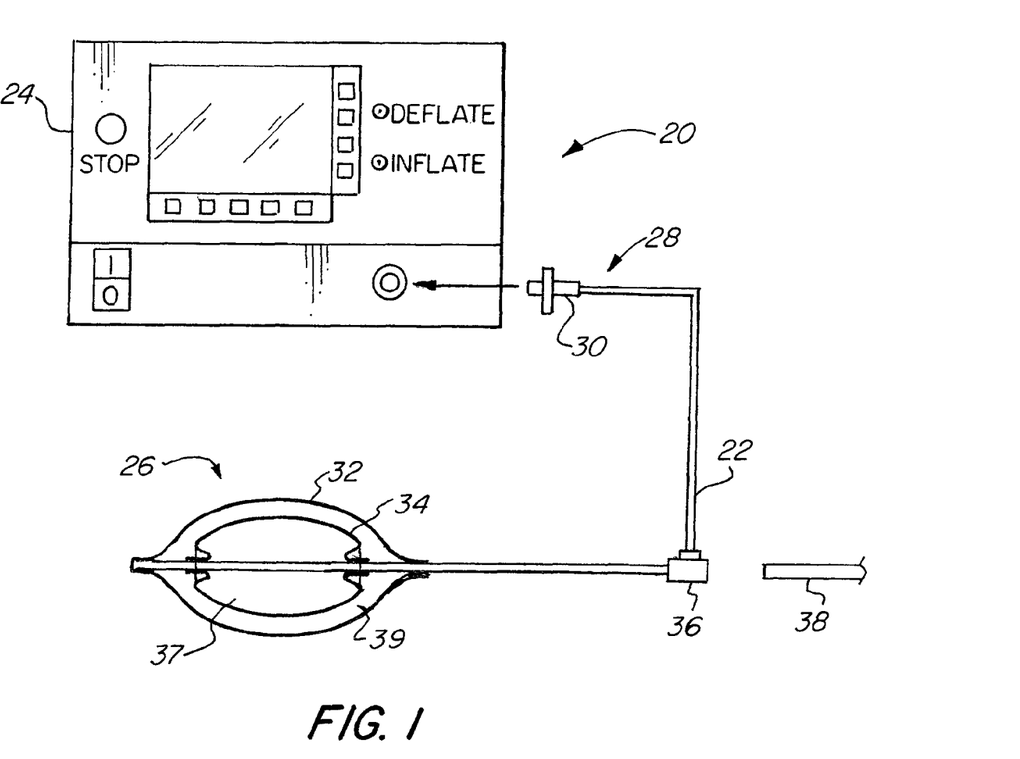
FIG. 1 is a schematic view of a nested balloon catheter system for delivering therapeutic and/or diagnostic agents in accordance with the invention.

The basic components of one embodiment of a nested balloon catheter system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1, the nested balloon catheter system (20) includes a catheter (22) and a fluid source (24). The catheter (22) may have any suitable diameter and length depending on a particular application, and may be flexible, rigid or semi rigid. The catheter (22) may be made with any commercially available material that is flexible enough to allow the shaft to be safely inserted through the available opening of a bodily cavity such that it will bend instead of puncturing the walls of the cavity, and at the same time is rigid enough such as it will maintain its shape as it is passed alongside and/or through the available opening of the bodily cavity. In an advantageous embodiment, the catheter (22) consists of a coil wire made of any suitable material, such as stainless steel, and a coating made of polyethylene. A distal end of the catheter (22) preferably includes a safety tip (not shown) that, when the catheter (22) is inserted into a bodily cavity, will bend instead of puncturing the walls of the cavity.

Any suitable fluid source may be used in accordance with the present invention. In the preferred embodiment shown in FIG. 1, the fluid source (24) is an electro-pneumatic pump having controls on the front thereof, from which a physician or assistant can control the system (as well as a remote control unit), such as that disclosed in U.S. Patent Application No. 2010/0121270 by Gunday et al., the specification of which is hereby incorporated by reference herein in its entirety. A proximal end (28) of the catheter (22) is connected to the pump (24) via a connection port (30). The port (30) is provided with any suitable connector, such as a luer connector, for connection to the pump. The pump (24) supplies a fluid, such as a gas, liquid, or mixture thereof, to the catheter (22). The pump (24) also includes a variety of capabilities for balloon identification, proper inflation/deflation of the balloons, and feedback measurements, many details of which are described in Gunday et al. In certain advantageous embodiments, the pump (24) further includes a vacuum source to evacuate fluid from the catheter (22).

In some embodiments, the catheter (22) includes a data device, which may, for example, be optical, RFID, flash memory, etc. As a result, the pump (24) is able to identify the type of catheter that is connected and read catheter characterization data (including pressure, volume, dimensions, etc.) included thereon, and then adjust its control accordingly based on user input.

The pump (24) also controls and regulates the pressure by monitoring and taking into account one or more vital signs of the patient, such as body temperature, heart rate, blood pressure, and respiratory rate. For example, in certain applications, it will be desirable to know the degree to which the lung is inflated at any given time in order to deliver a therapeutic and/or diagnostic agent at the right time. Similarly, in certain cases, it will be important to measure the systolic and diastolic blood pressure, and at appropriate times, apply a pressure that exceeds the systolic pressure in order to facilitate extravasation of an agent. In certain embodiments, the electro-pneumatic pump (24) interfaces with an external monitoring device to obtain and monitor the patient vital signs to control the applied balloon pressure and/or the timing of the drug delivery. In other cases, the monitoring device is located in the pump (24).

In an advantageous embodiment, the catheter (22) also includes a connection port (36) for insertion of an imaging device (38). The structure and operation of the imaging device is described in more detail below.

The nested balloon catheter system (20) also includes a double balloon construct positioned at a distal end (26) of the catheter (22). The double balloon construct consist of an outer balloon (32) and an inner balloon (34) at least partially disposed in the outer balloon. The balloons (32, 34) may be made of latex, Yulex, polyethylene, nylon or other suitable material, and may come in a variety of sizes and diameters, which allow the nested balloon catheter system (20) to be used in bodily cavities of various diameters and dimensions, such as large and small bronchial branches, sinuses, and blood vessels, having different types of tumors and tissues to be treated. In certain embodiments, the balloon surfaces include an inert coating, such as a biocompatible lubricant, that facilitates the flow of drugs and agents between the balloons.

The outer balloon (32) has a wall with at least one opening therethrough and an inner surface. The inner balloon (34) at least partially encloses an inflation chamber (37) into which fluid is supplied from the fluid source (24) to inflate the inner balloon (34). An outer surface of the inner balloon (34) defines a space (39) between the inner surface of the outer balloon (32) and the outer surface of the inner balloon (34). The therapeutic and/or diagnostic agent is supplied to the space (39) and is then delivered to tissue through the openings in the wall of the outer balloon (32).

In some advantageous embodiments, the outer balloon (32) has a textured outer surface that acts as a gripping surface for attachment to bodily tissues, such as blood vessel walls. In other advantageous embodiments, the outer surface of the outer balloon (32) has a micro-abrasion surface intended to abrade the airway or vessel walls to stimulate bleeding and to instigate leukocyte extravasation and perpetuate fluid extravasation when volumetric pressure or force is applied to the abraded surface of the vessel wall to neutralize hemodynamic shear forces and further stimulate the extravasation process and associated cellular absorption of the diagnostic and/or therapeutic agents into the adjacent tissues.

In the embodiments wherein the outer balloon (32) has the abrasive and/or gripping surface, the outer surface of the outer balloon (32) includes a fiber mesh affixed to the surface during the molding process, which produces outwardly-facing protrusions that assist in gripping tissue in the bodily cavity and/or that optimize the abrasion capability of the balloon. The fiber mesh may be made of lycra, polyurethane, nylon, nylon coated with other materials such as cotton, composite springs, or other appropriate material. In other embodiments, dimensional surface structures or inflatable sinuses that are encapsulated in the surface substrate of the outer balloon (32) may be used to produce the surface protrusions.

In an advantageous embodiment of the nested balloon catheter, the inner balloon (34) and the outer balloon (32) are not bonded together. The inner balloon (34) is bonded at one end to the catheter (22), and then is pulled over the bonded end. The same is done at the other end, such that the inner balloon (34) curves inward towards the bonded parts when inflated, as shown in FIG. 1. The outer balloon (32) is pulled away from the bonded parts such that the outer balloon (32) curves outwards upon inflation, as also shown in FIG. 1. Such design creates extra space between the inner balloon (34) and the outer balloon (32) for accommodating the therapeutic and/or diagnostic agent.

In certain advantageous embodiments, at least one of the balloons (32, 34) includes imaging markers, such as radio opaque rings, located at or near the ends thereof. Such markers can be selected and appropriately positioned in order to reflect the relevant waves of various imaging modalities (e.g., x-ray) in order to allow the use of such modalities to assist with the precise positioning of the balloons (32, 34). Similarly, the balloon or balloon mesh may include radiopaque material, such as a mesh made of yarn having radiopaque iron fibers.

Figure 2:
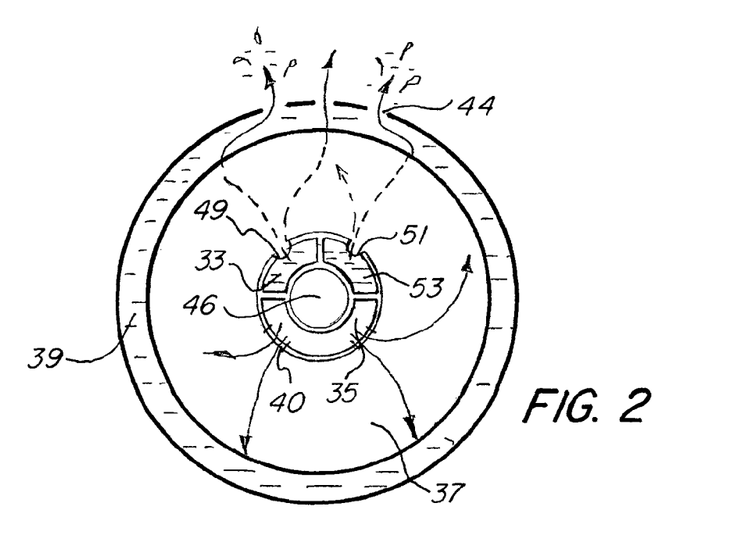
FIG. 2 is a cross-sectional view of the catheter assembly of FIG. 1.

The catheter (22) includes a first lumen (33) and a second lumen (35), as shown in FIG. 2. The first lumen (33) is in fluid communication with the space (39) between the inner surface of the outer balloon (32) and the outer surface of the inner balloon (34) via an opening (49). The first lumen is used to supply the therapeutic and/or diagnostic agent to the space (39), and then through the openings (44) in the wall of the outer balloon (32) into tissue in the bodily cavity. The second lumen (35) is in fluid communication with the inflation chamber (37) in the inner balloon (34) via at least one opening (40) in the catheter (22). The second lumen (35) is used to supply fluid from the fluid source (24) to the inflation chamber (37) to inflate the inner balloon (34).

The catheter (22) further includes a center lumen (46), which can be used to deliver any number of things to assist insertion and positioning of the nested balloon catheter system (20) within the bodily cavity and to carry out various medical procedures. It should be noted that additional lumens may be provided in the catheter (22) for introduction of various medical instruments to carry out various diagnostic or therapeutic procedures. The center lumen (46) can also be used as a bypass channel to allow bodily fluids, such as air or blood, to flow through the balloon catheter, which is necessary in certain medical applications, e.g. pulmonology or cardiology. Though not all are shown, the referenced lumens each terminate and are accessible at the proximal end of the catheter (26). In certain cases, the lumen (46) is connected at the proximal end to a respiratory device.

Figure 3A:
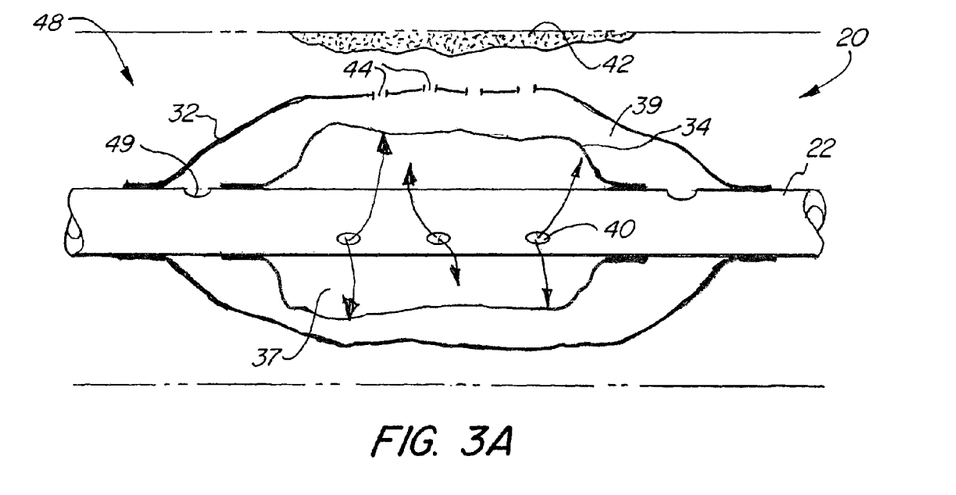
FIG. 3A is a partially exposed, isometric view of the catheter assembly of FIG. 1 positioned in a bodily cavity, showing the balloons in a deflated state.
Figure 3B:
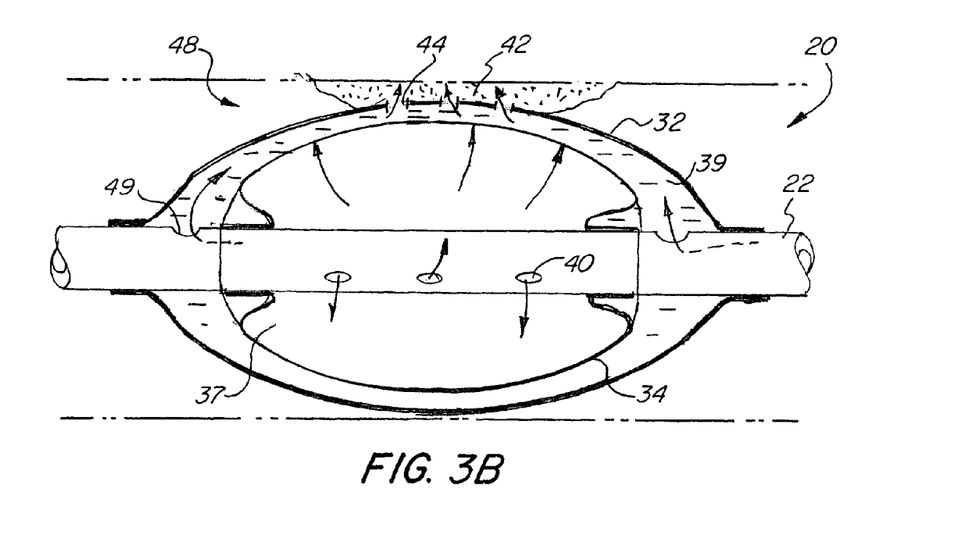
FIG. 3B is a partially exposed, isometric view of the catheter assembly of FIG. 1 positioned in a bodily cavity, showing the balloons in an inflated state.

FIGS. 3A and 3B illustrate a stepwise operation of the nested balloon catheter system (20) in a bodily cavity. The catheter assembly (22) is first inserted into a bodily cavity (48) until the double balloon construct (32, 34) is in the vicinity of the target site, which in this case is a tumor (42). As shown in FIG. 3A, once the catheter (22) reaches the desired position along the bodily cavity (48), fluid is supplied to the inflation chamber (37) via the lumen (35) in the catheter (22) through the plurality of openings (40) to inflate the inner balloon (34). It should be noted that, although the plurality of openings (40) in the catheter (22) in illustrated in FIG. 3A, one opening is sufficient to supply fluid to inflate the inner balloon (34).

As the inner balloon (34) becomes inflated, a therapeutic and/or diagnostic agent is supplied via the lumen (33) in the catheter (22) to the space (39) between the inner balloon (34) and the outer balloon (32). The agent is supplied through the openings (49) in the catheter (22) positioned within the space (39), such that the agent fills the space (39) between the balloons. As illustrated in FIG. 3B, the inner balloon (34) is continuously inflated and the therapeutic and/or diagnostic agent is urged out of the openings (44) in the wall of the outer balloon (32) and into the tumor tissue (42).

In the embodiment shown in FIG. 3B, the inner balloon (34) is fully inflated, such that the wall of the outer balloon (32) is pressed against the tumor tissue (42), which facilitates the absorption of the therapeutic and/or diagnostic agent into the tissue. However, it should be understood that the inner balloon (34) can be only partially inflated, such that the agent is pushed out of the openings in the outer balloon (32) into a space between the tumor tissue (42) and the wall of the outer balloon (32).

In some advantageous embodiments, the outer balloon (32) is also inflated by supplying fluid thereto by the fluid source (24) via an additional lumen in the catheter (22), separate from the lumen (33) used to supply the therapeutic and/or diagnostic agent. In these embodiments, the outer balloon (32) can be inflated such that the wall of the outer balloon (32) presses against the tumor tissue (42), and then the agent is delivered through the openings (44) into the tissue. This way, the agent can be delivered to a more precisely targeted area of the tissue. Additionally, the inflation of the outer balloon (32) can assist in anchoring the balloon assembly within the bodily cavity during the drug delivery process.

Any of various agents useful in therapeutic application can be delivered in the above described manner. For example, the agent may comprise one or more chemical or biological compounds with useful pharmacological properties, as well as any other compounds or other substances with medicinal or other therapeutic uses. Such agents may be synthetic or natural, so long as they have an advantageous therapeutic effect that can obtained by delivering the agent to a target site. In certain embodiments, agents particularly useful for chemotherapies, radiation therapies, or immunotherapies are delivered as described above.

In some advantageous embodiments, a cytotoxic substance or other agent useful for chemotherapy is delivered to a target site via the nested balloon catheter system of the present invention. For example, in some cases, the catheter system is used to deliver a chemical agent that affects cell division or DNA synthesis. Such agents include, for example, alkylating antineoplastic agents, such as cisplatin, carboplatin, oxaliplatin, mechlorethamine, carmustine, cyclophosphamide, chlorambucil, ifosfamide, busulfan, treosulfan, melphalan hydrochloride, thiotepa, and dacarbazine; anti-metabolites, such as azathioprine, mercaptopurine, thioguanine, fludarabine, pentostatin, cladribine, fluorouracil, floxuridine, cytosine arabinoside, gemcitabine, methotrexate, pemetrexed, and raltitrexed; anthracenedione antineoplastic agents, such as mitoxantrone; anthracyclines, such dactinomycin, daunorubicin, doxorubicin, epirubicin, idarubicin, valrubicin, aclarubicin, and bleomycin; plant alkaloids and terpenoids, such as noscapine, vincristine, vinblastine, vinorelbine, vindesine, podophyllotoxin, paclitaxel, and docetaxel; topoisomerase inhibitors, such as irinotecan, topotecan, amsacrine, etoposide, etoposide phosphate, and teniposide; and other agents with similar mechanisms of action, such as mitomycin C.

Other such agents include those that target molecular abnormalities, including tyrosine kinase inhibitors, such as crizotinib, gefitinib, erlotinib hydrochloride, imatinib, and imatinib mesilate. Still other such agents include those that modulate tumor cell behavior without actually attacking the cells, such as may be employed for hormone treatments. Indeed, any drug known to be efficacious in treating cancerous cells, such as streptozotocin or diltiazem augment taxol, may be employed.

In certain advantageous embodiments, a biological response modifier or other biological agent useful for immunotherapy is delivered to a target site via the balloon catheter system. Such agents, which are often cytokines, may be a recombinant, synthetic, or natural preparation. These biological agents may include, for example, interferons, such as alpha-interferons and beta-interferons; interleukins, such as aldesleukin; colony-stimulating factors, such as filgrastim, sargramostim, epoetin, and oprelvekin; monoclonal antibodies, such as edrecolomab, rituximab, trastuzemab, gemtuzumab, alemtuzumab, nimotuzumab, cetuximab, bevacizumab, ibritumomab, panitumumab, and tositumomab; cancer vaccines; gene therapies; and non-specific immunomodulating agents. Any biologic known to useful for immunotherapies, such as asparaginase, may be employed.

In some advantageous embodiments, the therapeutic agent is delivered in drug eluting microspheres, which can be used both to cause the embolization of blood vessels that supply undesirable tissues and to retain the drug in a localized area for a sustained period of time. For example, drug-eluting microspheres can be used to deliver a chemotherapeutic drug, such as doxorubicin, to a tumor. When the microspheres reach the target site, they will block vessels supplying the tumor, and this suppression of blood flow will lead to ischemia. Over time, the microspheres break down, and the drug will be absorbed by the tissue. As a result, not only is a localized sustained release of the drug achieved, but the ischemia will also increase the effect of the drug on the tumor.

The above described delivery of therapeutic agents is also useful for radiation therapies, in which high-energy radiation is used to kill cancer cells and shrink tumors. One method of such therapy places radioactive material in the body near the cancer cells. Thus, in certain advantageous embodiments, a radioactive substance, such as a radiolabeled monoclonal antibody, is supplied via the nested balloon catheter and extravasated into nearby tissue as described below.

Various agents may also be employed to assist in making diagnostic observations or monitoring procedures. For example, in some advantageous embodiments, the above described system may be used to deliver a contrast agent that allows or improves visualization via one or imaging modalities, which can be used to image the extravasation of the agent into the surrounding tissues throughout the course of a procedure. Such agents may include, for example, radiocontrast agents, such as iodine or barium, to improve X-ray based imaging techniques; MRI contrast agents, such as gadolinium, to improve magnetic resonance imaging; and microbubble contrast agents, to improve ultrasound imaging.

In some advantageous embodiments, biomarkers are used together with a therapeutic agent to observe and monitor the extravasation of the agent into the surrounding tissues. In some of these advantageous embodiments, CF3PM & MTFN-1 fluorinated radio-opaque biomarkers are used. The biomarkers may be detected by various non-invasive imaging modalities, such as X-Ray, MRI, CT, ultrasound, spectroscopy, etc.

With the addition of an appropriate inert dye or contrast media (e.g., radioactive, polarized, florescent, temperature sensitive) to a drug to be extravasated, the drug infusion rate and the amount of drug infused into the tissue can be monitored, quantified, and recorded/displayed, such as, for example, by capturing and storing sequential video frames under different illumination conditions (UV, IR, polarized, color filters, etc.). Further, by deploying a contrast agent along with a therapeutic agent, one may visually identify the extravasation depths and/or discern the requisite volumetric pressure, force, temperature, frequency and/or time to achieve efficacious delivery of the therapeutic agent to the desired depth of penetration at the intended treatment site.

As described above, in certain advantageous embodiments, the wall of the outer balloon (32) has an abrasive surface. In these embodiments, the inner balloon (34) is first fully inflated, such that the abrasive surface of the outer balloon (32) abrades the tissue to stimulate a flow of leukocytes to the target tissue site, and then the agent is delivered to tissue through the openings in the outer balloon (32). This stimulates extravasation and associated cellular absorption of the diagnostic and/or therapeutic agent into the tissue. Alternatively, the agent is first urged into tissue by inflation of the inner balloon (34), and then the inner balloon is repeatedly inflated and deflated to abrade the tissue with the abrasive surface of the outer balloon (32).

In further embodiments, after the therapeutic and/or diagnostic agent is urged out of the openings (44) in the outer balloon (32), the pump (24) supplies fluid to the inflation chamber (37) in pulsed fashion to repeatedly inflate and deflate the inner balloon (34). This causes a change in volumetric pressure exerted on a bodily lumen wall to neutralize hemodynamic shear forces and to stimulate extravasation of the therapeutic agent into tissue. As explained above, the pump can apply controlled pressure that is synchronized with the patient's vital signs.

The catheter (22) can have multiple lumens to supply therapeutic agents to the space (39) between the inner and outer balloons (32, 34), which allows for delivery of multiple agents separately, as may be desired when using two different pharmaceuticals that should not be mixed until just before being extravasated into bodily tissue. For example, as shown in FIG. 2, the catheter (22) can include two delivery channels (33) and (51), each supplying a different agent via the openings (49) and (53) respectively. Likewise, one may need to deliver one medicinal agent at the beginning of the procedure, and another medicinal agent at a later time during the procedure. In case where it is desirable to deliver two incompatible agents separately to prevent contamination, the space (39) between the balloons can be divided into several compartments, with each lumen leading to an opening into a separate compartment for delivery of a particular agent. Similarly, one may wish to deliver a second agent at a slightly different location than the first agent, which can be accomplished by providing two separate compartments between the balloons, for example one at the distal end of the balloons and the other at the proximal end of the balloons, and delivering each agent to tissue adjacent to each of the compartments.

In an advantageous embodiment, an imaging device disposed in one of the lumens of the catheter (22) can be used to help position the inner and outer balloons at the proper location. For example, the lumen (33) that delivers the therapeutic and/or diagnostic agent may be large enough to also accommodate the imaging device, such that the imaging device can exit one of the openings (49), through which the agent is delivered into the space (39) between the balloons. In this embodiment, the wall of the outer balloon (32) is transparent such that the imaging device can view the surrounding tissue through the wall.

In other embodiments, both the inner and outer balloons (32, 34) are transparent, and the imaging device can be introduced via the lumen (35), through which fluid is supplied to the inflation chamber (37) to inflate the inner balloon (34), out one of the openings (40) and into the inner balloon (34) in order to view the surrounding area through the transparent wall of the inner and outer balloons. Alternatively, an additional lumen can be provided in the catheter (22) to accommodate the imaging device, such as the center lumen (46), and this lumen can connect to an opening leading to the inside of the inner balloon (34) or to the space (39) between the inner balloon (34) and the outer balloon (32).

In some advantageous embodiments, the distal end of the catheter (22) includes a transparent membrane made out of any suitable material. The imaging device is extended through one of the lumens of the catheter to the membrane, which allows for visualization of the area ahead of the catheter (22). In this way, the physician can be provided with illuminated light and direct visual feedback of the area ahead of the balloon catheter, along the sides of the balloons, and/or behind the balloons.

In other advantageous embodiments, the lumen of the catheter (22), in which the imaging device is disposed, has an opening at a distal end, and the imaging device is extended out of the opening to visualize tissue in front of the nested balloon catheter system (20). In this embodiment, the catheter (22) can also be provided with a cleaning device at the distal tip for cleaning the imaging device. The cleaning device is made with any suitable type of material, such as textile bundle, and is affixed to an inner surface of the catheter (22) adjacent to the opening at the distal end. The imaging device is cleaned by moving it back and forth through the textile bundle, thus wiping a lens of the imaging device.

The imaging device can be any device suitable for viewing the target area, such as a coherent fiber bundle or appropriate optical element and lens assembly in conjunction with an imaging sensor (e.g., CMOS, CCD), having a sufficiently small outer diameters, such as, for example, 0.75 mm -1.5 mm. In some cases, the imaging device has a pre-shaped distal tip that enables it to easily extend through one of the aforementioned openings. The distal tip of the imaging device is preferably flexible such that it can be translated linearly or rotationally thereby allowing for 360° visualization of the surrounding area.

Figure 4:
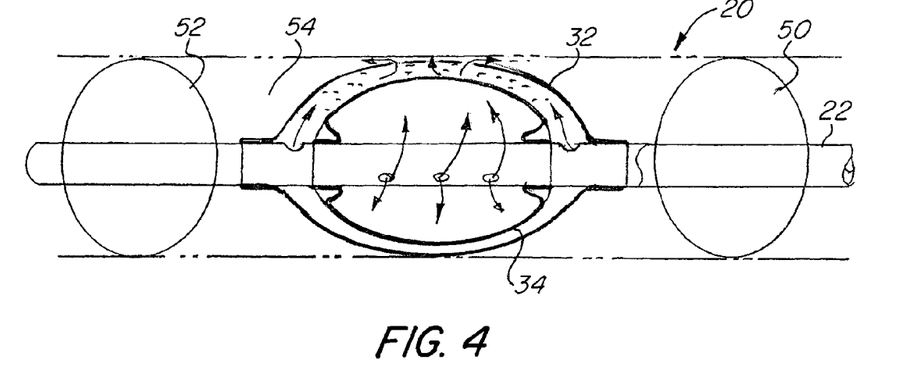
FIG. 4 is a partially exposed, isometric view of another embodiment of the catheter assembly of FIG. 1 positioned in a bodily cavity.

FIG. 4 illustrates another embodiment of the nested balloon catheter system of the present invention. In this embodiment, the catheter further includes a proximal balloon (50) and a distal balloon (52) positioned along the catheter (22) on both sides of the double balloon assembly (32, 34). The catheter includes two additional lumens, one in fluid communication with the proximal balloon (50) and the other in fluid communication with the distal balloon (52). It should be noted that a single lumen can be provided instead of the two lumens to supply fluid to both proximal and distal balloons.

In an advantageous embodiment, the proximal and distal balloons (50, 52) are provided with a textured surface that assists in gripping of the balloons to the surrounding tissue upon inflation to facilitate secure positioning of the balloons in the bodily cavity. The walls of the proximal and distal balloons (50, 52) can be made transparent to enable visualization via an imaging device disposed inside the balloons, as described above with respect to the inner and outer balloons.

Once the balloon catheter is introduced into a bodily cavity and positioned at a target site, the proximal balloon (50) and the distal balloon (52) are inflated by supplying fluid thereto by the pump (24) via the lumens, as discussed above. The proximal and distal balloons (50, 52) are inflated simultaneously to create a chamber therebetween (54), into which the therapeutic and/or diagnostic agents are delivered through the openings in the outer balloon (32). Alternatively, the distal balloon (52) is inflated first and is used as an anchor to secure the balloon catheter assembly at the target site, and then the proximal balloon (50) is inflated to create the chamber (54).

The chamber (54) functions to isolate the target treatment site from the surrounding tissue, which is particularly desirable during delivery of highly toxic chemotherapy agents to decrease exposure to such agents. Additionally, by creating the fluidly isolated chamber (54), it is possible to change volumetric pressure within the chamber to facilitate extravasation of the agent into target tissue. This can be achieved by repeatedly inflating and deflating the inner balloon (32) and/or the outer balloon (34) such that the fluid pressure in the chamber (54) is increased and decreased.

Once the agents have been delivered and extravasted into the tissue at the target site, any remaining agent can be evacuated from the chamber (54) via the same openings and lumens through which they were supplied to the chamber (54) using suction. In certain advantageous embodiments, the fluid source (24) produces a negative pressure to vacuum out the agents. Alternatively, additional lumens and corresponding openings may be employed in the manner previously described to evacuate the agents through lumens different from those used to supply the agents to the chamber (54). Regardless, the various lumens and corresponding openings can be used to cyclically deliver and evacuate the agents and various other fluids instantly, sequentially, intermittently and/or continuously over designated time intervals.

In some embodiments, one of the lumens of the catheter (22) is used to supply an irrigation fluid. For example, when using both a therapeutic agent and a contrast agent, once the contrast agent has reached, and sufficiently saturated, the intended treatment site, any remaining contrast agent can be vacuumed out of the chamber (54). The chamber (54) can then be irrigated, lavaged, and suctioned to remove any residual agent.

The therapeutic and/or diagnostic agent can be delivered to the lumen (33) via any suitable mechanism. In one advantageous embodiment shown in FIG. 5, the therapeutic and/or diagnostic agent is contained in a drug capsule (56) adapted to be positioned into a delivery apparatus (58). The drug capsule (56) is prefilled with the agent and is sealed at a distal end by a piercable membrane (62) and at a proximal end by a slidable piston (64). The capsule (56) can be made out of any suitable material, and preferably is transparent such that the amount of the agent delivered can be monitored. The size of the drug capsule (56) and the amount of the agent it can hold can be variable depending on a particular application. For example, the capsule (56) can be filled with the amount of the agent to be delivered plus the amount needed to prime the drug delivery lumen (33) of the catheter (22). The drug delivery lumen (33) can also be primed before the catheter (22) is deployed to the target area.

Figure 5:
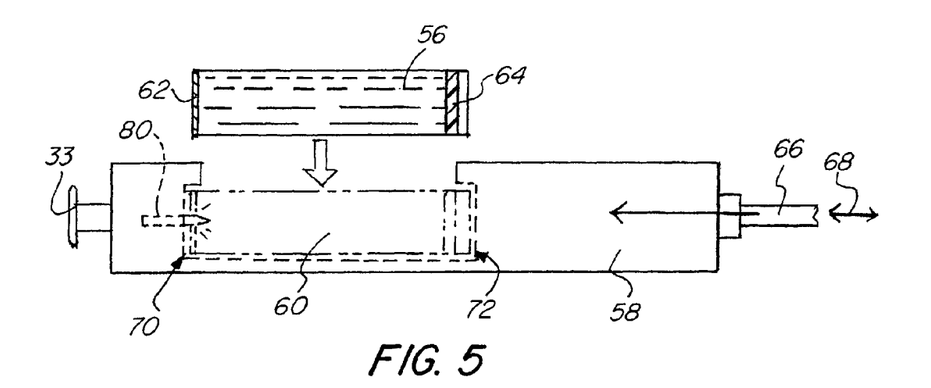
FIG. 5 is a schematic view of a delivery mechanism of the catheter assembly of FIG. 1.

The drug capsule (56) fits into a capsule compartment (60) of the delivery apparatus (58), which is connected to the delivery lumen (33) at a distal end and is connected to a fluid source (68) at a proximal end via a lumen (66). The fluid source (68) can be the same pump that is used to inflate the inner balloon or can be a separate pump. A distal end (70) of the capsule compartment has a needle (80) or any other suitable piercing device that functions to pierce the membrane (62) of the capsule (56). A proximal end (72) of the capsule compartment has an actuation mechanism adapted to actuate the piston (64) of the capsule (56). The capsule compartment (60) is preferably made out of transparent material such that the location of the piston can be determined and therefore the amount of the agent delivered can be observed and monitored.

The capsule (56) filled with the therapeutic and/or diagnostic agent is first positioned into the capsule compartment (60) of the delivery apparatus (58), such that the membrane (62) is pierced by the needle (80) located at the distal end (70) of the capsule compartment (60) to allow the agent to exit out towards the delivery lumen (33). Once the drug capsule (56) is securely positioned inside the capsule compartment (60), the actuation mechanism actuates the piston (64) such that it moves towards the distal end of the capsule (56), ejecting the therapeutic and/or diagnostic agent out of the capsule into the delivery lumen (33) of the catheter (22). If the agent to be delivered to tissue is in gaseous form, the delivery apparatus (58) can further include a valve (not shown) positioned at the distal end of the apparatus before the connection to the drug delivery lumen (33). The valve controls how much gaseous agent is delivered to the lumen (33), as well as the delivery time.

The actuator mechanism of the delivery apparatus (58) can be a pneumatic cylinder, into which fluid is supplied by the fluid source (68), wherein fluid pressure pushes the piston (64) forward, ejecting the agent out of the capsule (56). In other embodiments, the actuator mechanism can be an electrical motor, e.g. a stepper or a servo motor. The actuator mechanism is connected to a controller that controls the quantity of the agent to be delivered and the delivery time period. The controller can be pre-programmed to deliver the exact quantity of drug over the exact amount of time, or it can be operated manually by the user during the procedure.

The piston (64) is preferably provided with a sensor, e.g. a magnetic sensor, mechanical or optical encoder, or any other suitable type of sensor, so that the position of the piston can be detected and communicated to the controller, which then determines how much drug has been delivered. A pressure transducer can also be provided at the distal end of the delivery apparatus (58) for measuring pressure in the drug delivery lumen (33) and reporting it to the controller that regulates the drug delivery rate with the balloon pressures and detects any problems that may arise. The controller also regulates and modulates the inflation and deflation of the inner balloon.

It should be noted that other embodiments of the drug delivery mechanism can be used without departing from the spirit of the present invention. The drug capsule prefilled with the agent to be delivered can be primed at any location along the catheter (22), such as, for example, adjacent to the balloons (32, 34). The capsule can be disposed in the outer housing of the catheter or in any of the catheter lumens.

Figure 6A:
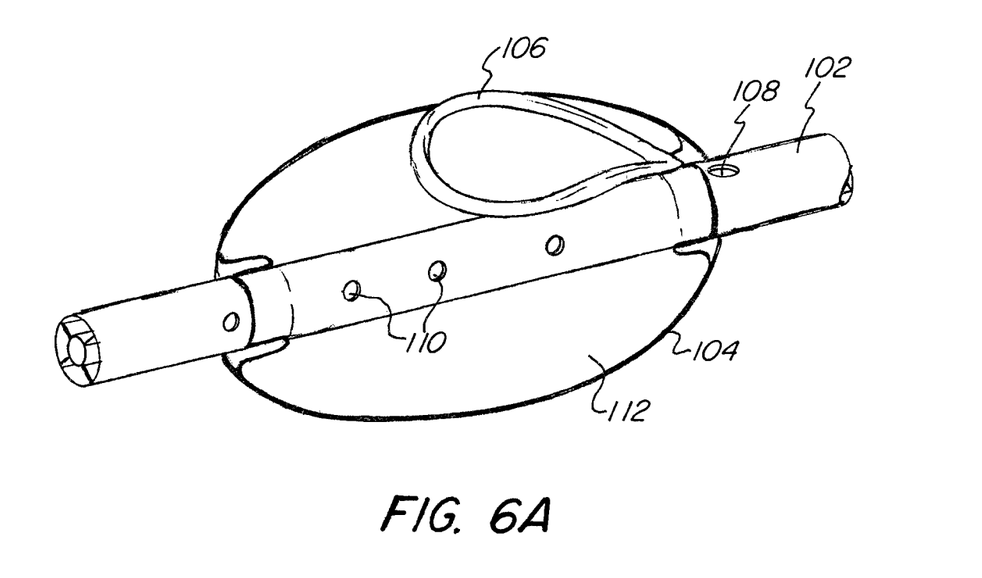
FIGS. 6A-6D illustrate an alternative embodiment of the catheter assembly of FIG. 1.

FIGS. 6A-6D illustrate another advantageous embodiment of the inner balloon and the outer balloon of the nested balloon catheter system. FIG. 6A illustrates a portion of a catheter (102) with an inner balloon (104) disposed thereon. A wall of the inner balloon (104) has an inner surface and an outer surface, and at least partially encloses an inflation chamber (112). The catheter (102) includes a plurality of openings (110), through which fluid is supplied from a fluid source to the inflation chamber (112) via one of the catheter lumens to inflate the inner balloon (104). The catheter also includes at least one opening (108) positioned outside of the inner balloon (104), through which a therapeutic and/or diagnostic agent is supplied via another lumen of the catheter (102). The outer surface of the inner balloon's wall has a protrusion (106) extending above the wall surface. The protrusion (106) has a tear-drop shape terminating at the distal end of the inner balloon (104) adjacent to the opening (108).

Figure 6B:
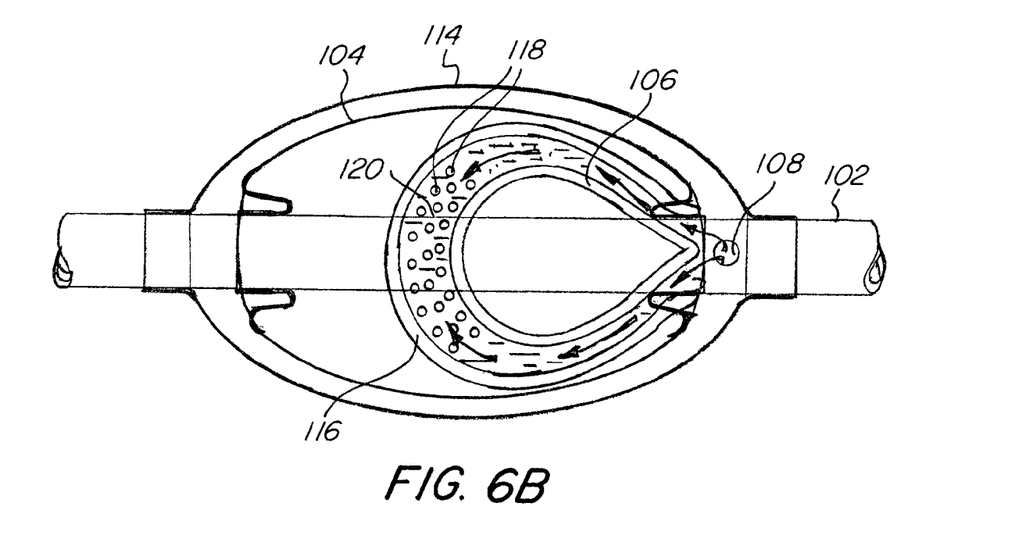

FIG. 6B illustrates a top view of the catheter assembly (102), showing both the inner balloon (104) and an outer balloon (114). A wall of the outer balloon (114) has a protrusion (116) on an inner surface, extending beyond the inner surface of the outer balloon (116) towards the outer surface of the inner balloon (104). The protrusion (116) is shaped such that it corresponds to the shape of the protrusion (106), forming a channel (120) defined by the two protrusions (106, 116) between the inner surface of the outer balloon (114) and the outer surface of the inner balloon (104). The wall of the outer balloon (114) has a plurality of openings (118) positioned adjacent to the channel (120). When the therapeutic and/or diagnostic agent is supplied to the space between the two balloons (104, 114) through the opening (108) in the catheter (102), the agent flows through the channel (120) and is then urged out of the openings (118) into adjacent tissue.

Figure 6C:
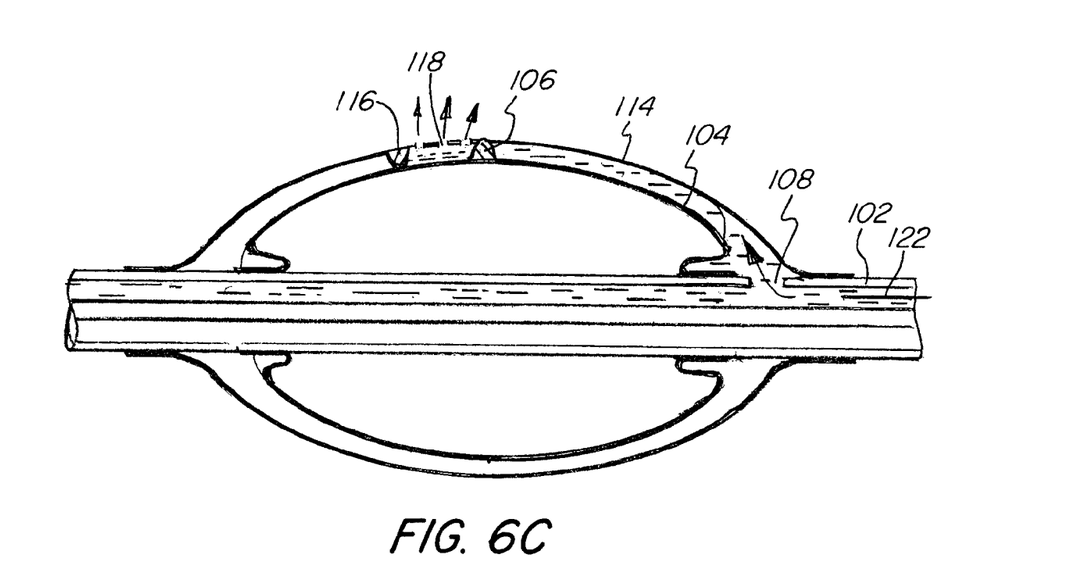
Figure 6D:
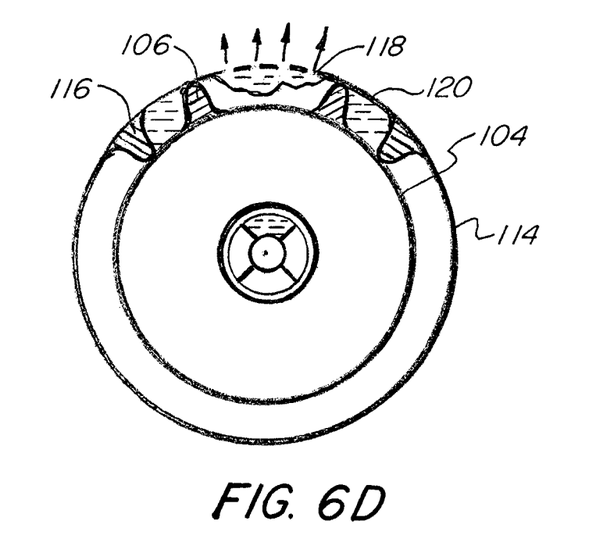

This is further illustrated in FIGS. 6C and 6D, which show longitudinal and transverse cross-sectional views of the catheter assembly (102). The therapeutic and/or diagnostic agent is delivered via a catheter lumen (122) through the opening (108) and into the space between the inner balloon (104) and the outer balloon (114). The agent collects in the channel formed by the protrusion (106) on the outer surface of the inner balloon (104) and the protrusion (116) on the inner surface of the outer balloon (114). As the inner balloon (104) is inflated, the agent is pushed out of the openings (118) into the tissue. Such design allows for more precise delivery of the agent to the targeted tissue by preventing or minimizing the agent from exiting the targeted tissue area.

The protrusions (106, 116) on the inner balloon (104) and the outer balloon (114) are formed during the balloon manufacturing process. For example, a mandrel used during the balloon molding process can have depressions that correspond to the desired protrusions to be formed on the surface of the balloons. When the mandrel is dipped into the balloon material, such as latex or yulex, the material fills the depressions. The formed balloon is then removed from the mandrel and turned inside out such that the excess material in the depressions is now on the outside surface of the balloon, forming the protrusions.

Figure 7A:
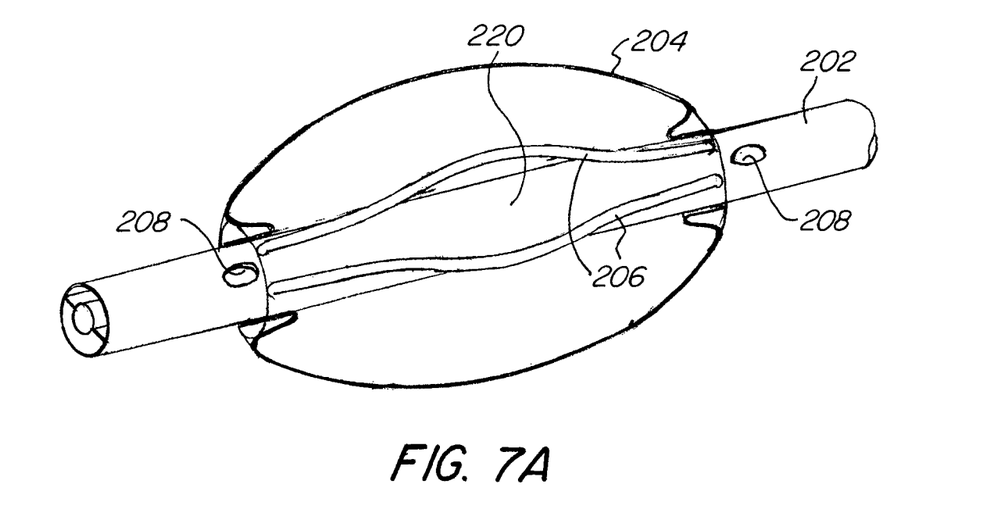
FIGS. 7A-7D illustrate another alternative embodiment of the catheter assembly of FIG. 1.

FIGS. 7A-7D illustrate an additional embodiment of the double balloon construct of the present invention. In this embodiment, as shown in FIG. 7A, an inner balloon (204) has length-wise protrusions (206) on the outer surface of the balloon that run from a distal end to a proximal end of the balloon. The protrusions (206) form a channel (220) therebetween that originates and terminates at openings (208) in the catheter (202) through which the agent is supplied. The middle section of the channel (220) is wider to allow the agent to pool in that section.

Figure 7B:
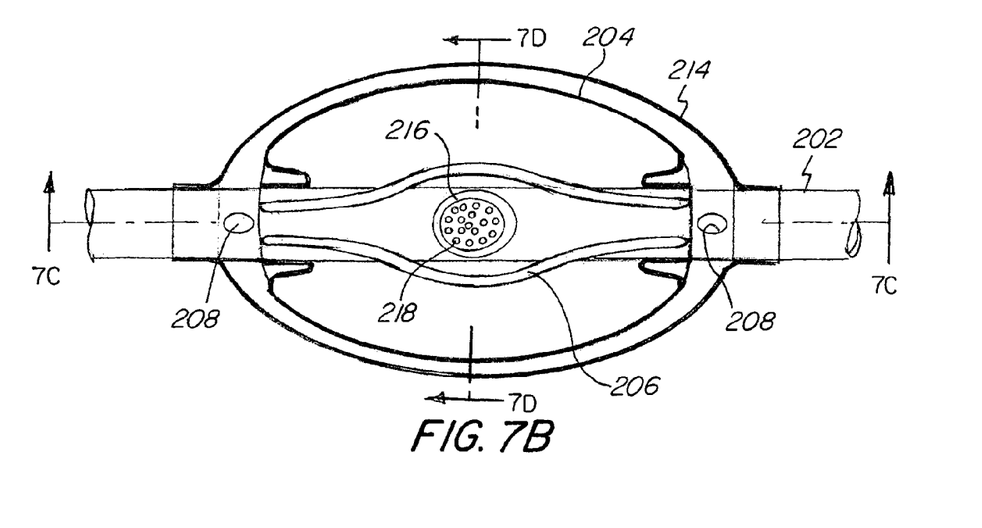
Figure 7C:
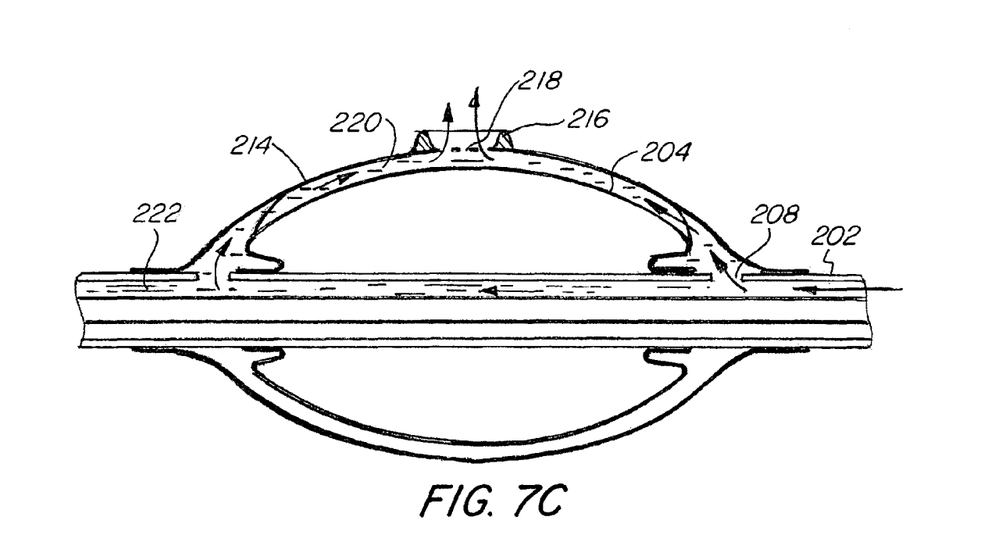
Figure 7D:
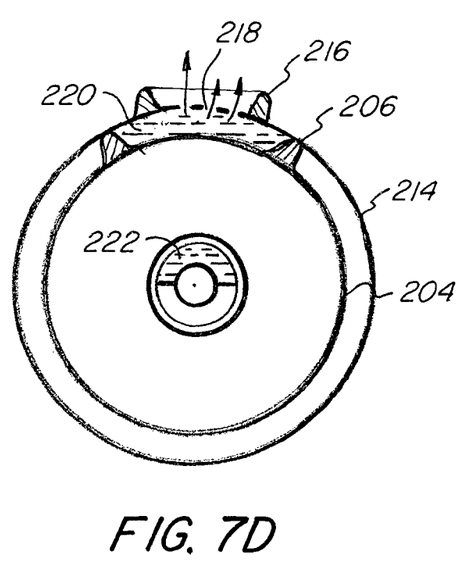

An outer balloon (214) has a circular protrusion (216) provided on the outer surface of the balloon (214) and extending outwardly from the balloon (214), as illustrated in FIG. 7B. A wall of the outer balloon (214) has perforations (218) in the area inside the circular protrusion (216). As shown in FIGS. 7C and 7D, the therapeutic and/or diagnostic agent is delivered via a catheter lumen (222) through the openings (208) into the space between the inner balloon (204) and the outer balloon (214). The agent is directed through the channel (220) and collects in the wider section of the channel. The inner balloon (204) is inflated such that the circular protrusion (216) of the outer balloon (214) is pressed against the target tissue area and the agent is pushed out of the openings (218) into the target tissue. The circular protrusion (216) assists in containing the agent within an isolated area such that it is delivered directly to the target tissue area.

It should be understood that the embodiments depicted in FIGS. 6A-6D and 7A-7D are only illustrative and that other configurations of the balloons can be used without departing from the spirit of the invention. For example, the protrusions can be provided only on the surface of the inner balloon or only the surface of the outer balloon. Further, the protrusions can have any desirable shape and configuration depending on where the therapeutic and/or diagnostic agent needs to be delivered.

The nested balloon catheter system (20) of the present invention can also be used to supply various media, e.g. light based therapies, radiofrequency wave forms, thermal energies and temperatures, and pressured air, to modulate cellular response sufficient to achieve tumoral destruction and to alter cellular membrane integrity to facilitate extravasation of medicinal and/or diagnostic agents into bodily tissues.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A balloon catheter for delivering a therapeutic and/or diagnostic agent to tissue, comprising:
    an outer balloon having a wall with at least one opening therethrough and an inner surface;
    an inner balloon at least partially disposed in said outer balloon, said inner balloon at least partially enclosing an inflation chamber and having an outer surface defining a space between the outer surface of said inner balloon and the inner surface of said outer balloon;
    a catheter having
        a first lumen in fluid communication with the space between the outer surface of said inner balloon and the inner surface of said outer balloon for supplying a therapeutic and/or diagnostic agent thereto; and
        a second lumen through which fluid is supplied to the inflation chamber of said inner balloon for inflating said inner balloon to urge the therapeutic and/or diagnostic agent out of the at least one opening in the wall of said outer balloon and into tissue;
    wherein at least one of said outer balloon and said inner balloon comprise at least one protrusion for directing the therapeutic and/or diagnostic agent; and
    wherein the at least one protrusion is formed by at least one of an inner balloon wall and the outer balloon wall.

2. The balloon catheter of claim 1, wherein the wall of said outer balloon has an abrasive outer surface for abrading tissue.

3. The balloon catheter of claim 1, further comprising a fluid source that supplies fluid to the second lumen of the catheter.

4. The balloon catheter of claim 2, wherein said fluid source comprises an electro-pneumatic pump.

5. The balloon catheter of claim 4, further comprising a monitoring device for monitoring at least one patient vital sign, wherein said pump controls the pressure to which the inner balloon is inflated based at least in part on the monitored vital sign.

6. The balloon catheter of claim 4, further comprising a monitoring device for monitoring at least one patient vital sign, wherein said pump controls the supply of the therapeutic and/or diagnostic agent based at least in part on the monitored vital sign.

7. The balloon catheter of claim 4, wherein said pump supplies fluid to said inflation chamber in pulsed fashion to repeatedly deflate and inflate said inner balloon.

8. The balloon catheter of claim 1, wherein said fluid source further comprises a vacuum source that evacuates fluid from the inflation chamber.

9. The balloon catheter of claim 1, further comprising an imaging device disposed in said catheter for viewing tissue in a bodily cavity.

10. The balloon catheter of claim 1, further comprising at least one imaging marker mounted adjacent to said inner and outer balloons.

11. The balloon catheter of claim 1, wherein said catheter has a distal end with an opening therein and wherein said catheter has a third lumen in fluid communication with the opening for passing bodily fluids through the catheter.

12. The balloon catheter of claim 1, further comprising at least one sensor for measuring at least one characteristic of tissue.

13. The balloon catheter of claim 1, further comprising a distal balloon positioned distally of said inner and outer balloons and a proximal balloon positioned proximally of said inner and outer balloons, wherein said fluid source inflates the proximal balloon and the distal balloon by supplying fluid thereto to create a chamber therebetween.

14. The balloon catheter of claim 13, wherein an outer surface of the proximal and distal balloons comprises a textured surface for preventing slippage of the outer surface on tissue.

15. The balloon catheter of claim 1, wherein said fluid is a gas.

16. The balloon catheter of claim 1, wherein the at least one protrusion comprises a protrusion on the inner surface of said outer balloon.

17. The balloon catheter of claim 1, wherein the at least one protrusion comprises a protrusion on the outer surface of said inner balloon.

18. The balloon catheter of claim 1, wherein said outer balloon has an outer surface and wherein the at least one protrusion comprises a protrusion on the outer surface of said outer balloon.

19. The balloon catheter of claim 1, wherein the at least one protrusion comprises a first protrusion having a shape on the inner surface of said outer balloon and a second protrusion corresponding to the shape of the first protrusion on the outer surface of said inner balloon to create a channel therebetween.

20. The balloon catheter of claim 1, wherein the wall of said outer balloon has an outer surface comprising a mesh sleeve of elastic yarn.

21. The balloon catheter of claim 20, wherein the mesh sleeve is radiopaque.

22. The balloon catheter of claim 1, wherein the agent is doxorubicin.

23. The balloon catheter of claim 1, wherein the agent is cisplatin, and wherein the method further comprises the step of supplying a second agent, said second agent being epinephrine.

24. The balloon catheter of claim 1, wherein the agent is 5-4 fluorouracil.

25. The balloon catheter of claim 1, wherein the agent is noscapine.

26. The balloon catheter of claim 1, wherein the agent is diltiazem augment taxol.

27. The balloon catheter of claim 1, wherein the agent is crizotinib.

28. The balloon catheter of claim 1, wherein the agent is erlotinib hydrochloride.

29. The balloon catheter of claim 1, wherein the agent is gefitinib.

30. The balloon catheter of claim 1, wherein the agent comprises drug eluting microspheres.

31. The balloon catheter of claim 30, wherein the drug eluting microspheres contain doxorubicin.

32. The balloon catheter of claim 1, wherein the agent is a combination of at least one therapeutic agent and at least one biomarker.

33. The balloon catheter of claim 32, wherein the biomarker is a radio-opaque marker.

34. A method of localized delivery of a therapeutic and/or diagnostic agent to tissue, comprising the steps of:

inserting a catheter into a bodily cavity, said catheter comprising an outer balloon having a wall with at least one opening therethrough and an inner surface; and an inner balloon at least partially disposed in said outer balloon, said inner balloon at least partially enclosing an inflation chamber and having an outer surface defining a space between the outer surface of said inner balloon and the inner surface of said outer balloon;

supplying the therapeutic and/or diagnostic agent to the space between the outer surface of said inner balloon and the inner surface of said outer balloon via a first lumen of said catheter;

inflating said inner balloon by supplying fluid to the inflation chamber via a second lumen of said catheter to urge the therapeutic and/or diagnostic agent out of the at least one opening in the wall of said outer balloon and into tissue; and directing the therapeutic and/or diagnostic agent to a localized area in the bodily cavity via at least one protrusion formed by at least one of an inner balloon wall and the outer balloon wall.

35. The method of claim 34, wherein the at least one protrusion comprises a first protrusion formed by the inner surface of said outer balloon and a second protrusion formed by the outer surface of said inner balloon, the first and second protrusions defining a channel, and wherein the step of directing the therapeutic and/or diagnostic agent to the localized area in the bodily cavity comprises supplying the agent to the channel.

36. The method of claim 34, wherein the wall of said outer balloon has an abrasive outer surface, and wherein the step of inflating said inner balloon comprises contacting tissue in the bodily cavity with the abrasive surface such that it abrades the tissue.

37. The method of claim 34, wherein the step of delivering the therapeutic and/or diagnostic agent to tissue further comprises inflating said inner balloon until the wall of said outer balloon contacts tissue in the bodily cavity.

38. The method of claim 34, wherein the step of inflating said inner balloon comprises supplying fluid thereto with an electro-pneumatic pump.

39. The method of claim 34, further comprising the step of using an imaging device disposed in said catheter to visualize tissue in the bodily cavity.

40. The method of claim 34, further comprising the step of measuring at least one characteristic of tissue in the bodily cavity via at least one sensor.

41. The method of claim 34, wherein said catheter further comprises a distal balloon positioned distally of said inner and outer balloons and a proximal balloon positioned proximally of said inner and outer balloons, wherein the method further comprises the step of inflating the distal and proximal balloons by supplying fluid thereto via at least one additional lumen of said catheter to create a chamber between the distal and proximal balloons, and wherein the step of delivering the therapeutic and/or diagnostic agent comprises delivering the agent to said chamber.

42. The method of claim 34, wherein the wall of said outer balloon has an outer surface comprising a mesh sleeve of elastic yarn.

43. The method of claim 42, wherein the mesh sleeve is radiopaque.

* * * * *